United States Patent [19]

Samour et al.

[11] 3,936,492

[45] Feb. 3, 1976

[54] MONOMERIC EMULSION STABILIZERS

[75] Inventors: Carlos M. Samour, Wellesley Hills; Mildred C. Richards, Wakefield, both of Mass.

[73] Assignee: The Kendall Co., Walpole, Mass.

[22] Filed: Aug. 9, 1974

[21] Appl. No.: 496,320

Related U.S. Application Data

[62] Division of Ser. No. 272,282, July 17, 1972, abandoned, which is a division of Ser. No. 867,899, Oct. 20, 1969, Pat. No. 3,780,092.

[52] U.S. Cl. ........... 260/482 R; 260/471 A; 260/470
[51] Int. Cl.² ......................................... C07C 87/30
[58] Field of Search ........ 260/485 H, 482 R, 471 A, 260/470

[56] References Cited
UNITED STATES PATENTS
3,882,162   5/1975   Clayton .......................... 260/471 A FOREIGN PATENTS OR APPLICATIONS
587,244   4/1947   United Kingdom ............. 260/471 A

*Primary Examiner*—Lorraine A. Weinberger
*Assistant Examiner*—Jane S. Myers

[57] ABSTRACT

A novel class of monomeric emulsion stabilizers consists of certain types of ethylenically-unsaturated radicals covalently linked to a quaternary nitrogen atom which in turn is covalently linked to a lipophilic radical. Such monomers will polymerize with other ethylenically-unsaturated radicals forming self-stabilized, surfactant-free polymeric dispersions.

3 Claims, No Drawings

MONOMERIC EMULSION STABILIZERS

This is a division of copending application Ser. No. 272,282, filed July 17, 1972, now abandoned, which in turn is a division of our application Ser. No. 867,899, filed Oct. 20, 1969, now U.S. Pat. No. 3,780,092.

This invention relates to stabilizing agents for emulsion polymerization. More particularly it relates to a class of quaternized organic salts which serve simultaneously as stabilizing agents for emulsion polymerizations and as monomeric reactants in the polymerization, so that the salts become an integral part of the polymer, which is thereby self-stabilized without the use of surfactants.

Polymeric latices, derived from ethylenically-unsaturated monomers, are widely used for a variety of applications, such as adhesive masses and binders for nonwoven fabrics. Most conventional polymeric latices are produced by an emulsion polymerization process, in which monomeric materials are polymerized while they are dispersed in an aqueous medium by means of a surface active agent. The surface active agent may be anionic in nature, such as soap or sodium lauryl sulfate. Alternatively, it may be of nonionic type as represented by various ethylene oxide derivatives, or by polyhydroxy compounds, or it may be cationic, as represented by alkyl ammonium halides. Cationic agents are preferably combined with a nonionic agent for improved performance. The polymerization of monomeric materials is also frequently effected in the presence of water-soluble protective colloids or stabilizing agents. Any of the above emulsifying or stabilizing agents leads to the presence of a water-sensitive ingredient in the final polymeric latex. For latex utilizations wherein wet strength and resistance to the influence of water are desirable, as in most paper coatings nonwoven fabrics, certain pressure-sensitive adhesive tapes, and the like, the presence of a water-sensitive ingredient in the polymeric mass is undesirable.

A preferred method of avoiding the presence of water-sensitive elements in a polymeric latex is to employ what is termed herein monomeric emulsion stabilizers — that is, a class of organic monomer which co-polymerize with the ethylenically-unsaturated monomers, becoming a part of the final polymer, but which stabilize the polymerization process against the formation of coagulum and against subsequent phase separation. Such monomeric emulsion stabilizers may be cationically-charged nitrogen compounds as set forth in my U.S. Pat. No. 3,399,159 wherein the use of monomers such as vinyl pyridines, acid-amines, and certain nitrogencontaining acrylic derivatives is described.

Also, in my copending application Ser. No. 769,355, filed Oct. 21, 1968, there is described a process for preparing monomeric emulsion stabilizers containing a quaternized nitrogen atom ionically linked to an acidic group, such as a sulfate, sulfite, sulfonate, or phosphate, which acid group is covalently bonded to a lipophilic group of 8 to 24 carbon atoms.

It is an object of the present invention to prepare a new and useful class of monomeric emulsion stabilizers containing a quaternized nitrogen atom covalently linked to an ethylenically unsaturated radical and to a lipophilic group, and ionically linked to an anionic group.

It is a further object of the invention to prepare a new and useful species of self-stabilized, surfactant-free polymeric emulsion suitable for use as coatings, binding agents for nonwoven fabrics, adhesives, and the like. Other objects of the invention will be apparent from the following specification and claims.

It has now been found that the polymerization of ethylenically unsaturated monomers may be advantageously carried out if a major portion of such a monomer or mixture of monomers is copolymerized with a minor proportion of a quaternized monomer of the general formula:

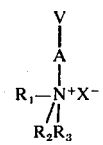

where V is an ethylenically-unsaturated radical selected from the following three classes:

a. acid ester groups or acid amido groups derived from the dicarboxylic unsaturated acids maleic, fumaric, citraconic, or itaconic, such as HO—CO—CH=CH—COO—, HO—CO—CH=CH—CONH—, HO—CO—CH=C(CH$_3$)—COO—, HO—CO—CH=C(CH$_3$)—CONH—, HO—CO—CH$_2$—C—COO—, and HO—CO—CH$_2$—CH—CONH—;
    ‖                              ‖
    CH$_2$                          CH$_2$ b. acrylic ester or acrylamido groups represented by the formulas CH$_2$=CR$_4$—COO— and CH$_2$=CR$_4$—CONH—, where R$_4$ is H or CH$_3$;

c. allyl, CH$_2$=CH—CH$_2$—; methallyl, CH$_2$=C(CH$_3$)—CH$_2$—; vinyloxy, CH$_2$=CH—O—; allyloxy, CH$_2$=CH—CH$_2$—O—; methallyloxy, CH$_2$=C(CH$_3$)—CH$_2$—O—; vinyl acetoxy, CH$_2$=CH—O—CO—CH$_2$—; allyl acetoxy; CH$_2$=CH—CH$_2$—O—CO—CH$_2$—; and methallyl acetoxy, CH$_2$=C(CH$_3$)—CH$_2$—O—CO—CH$_2$—.

In the formula given above, the A moiety of the monomeric emulsion stabilizer is zero when V is allyl, methallyl, vinyl acetoxy, allyl acetoxy, or methallyl acetoxy. Otherwise, A is a divalent radical selected from the classes consisting of a. ethylene, —CH$_2$—CH$_2$—; propylene, —CH$_2$—CH$_2$—CH$_2$—; hydroxypropylene, —CH$_2$—CHOH—CH$_2$—; acetoxypropylene,

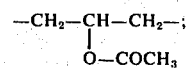

and isopropylene, —CH$_2$—CH(CH$_3$)—, ethylene, propylene, isopropylene, and hydroxypropylene being preferred;

b. —O—CH$_2$—CHR$_4$(O—CH$_2$—CHR$_4$)$_n$— where $n$ equals zero to four and R$_4$ again is H or CH$_3$.

The quaternary nitrogen group -N$^+$.R$_1$.R$_2$.R$_3$ contains a lipophilic radical R$_3$. By the term lipophilic radical in the claims and specification herein is meant a radical containing an aliphatic hydrocarbon chain having from about 7 to 28 carbon atoms, with a chain of 9 to 18 carbon atoms preferred. This hydrocarbon group may be covalently linked to the nitrogen either directly or through one of the following intermediate linkages; a benzyl group; an ester group such as —CH$_2$—CH- $_2$—O—CO—R$_3$; a polyalkylene oxide group such as —O—CH$_2$—CHR$_4$—(O—CH$_2$—CHR$_4$)n—OR$_3$ where R$_4$ is H or CH$_3$ and $n$ is 0 to 4; an alkyl acetoxy or alkyl acetamido group such as —CH$_2$—CO—OR$_3$ and —CH$_2$—CO—NHR$_3$; alkyl alkylene ethers such as —CH$_2$—O—R$_3$; and alkyl amides such as —CH$_2$—CH(CH$_3$)—NH—CO—R$_3$. The lipophilic radical R$_3$ may be linear or branched, saturated or unsaturated.

In the preferred embodiments of the invention, R$_1$ is an alkyl or benzyl group of from 1 to 7 carbon atoms, and R$_2$ is either an alkyl or benzyl group of from 1 to 7 carbon atoms or a group selected from the class consisting of R$_5$—O—CO—CH$_2$— and R$_5$—NH—CO—CH$_2$— where R$_5$ is H or an alkyl group of from 1 to 4 carbon atoms. Cases where R$_1$ and R$_2$ are lower alkyl groups, especially methyl groups, are preferred.

R$_1$ and R$_2$ may also be valence bonds of a cyclic amine of the piperidine or morpholine type,

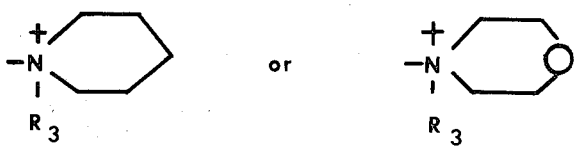

In the monomeric emulsion stabilizers of this invention, the X which is ionically linked to the quaternary nitrogen is an acid radical selected from the class consisting of F$^-$, Cl$^-$, Br$^-$, I$^-$, CH$_3$SO$_4^-$, C$_2$H$_5$SO$_4^-$, and

with Cl$^-$, Br$^-$, or CH$_3$SO$_4$ preferred.

Typical reaction procedures for producing the monomeric emulsion stabilizers of this invention include the reaction of an appropriate ethylenically-unsaturated alkylene halide with a tertiary amine containing a lipophilic group or with an appropriate ring compound in which nitrogen is a ring member; or the reaction of a halogenated compound containing active halogen with an ethylenically-unsaturated compound containing a tertiary amine.

Representative preparations are the reactions between allyl chloride and dimethyl dodecyl amine or dimethyl hexadecyl amine; between allyl bromide and N-cocomorpholine, in which the nitrogen atom in the morpholine ring is covalently bonded to a mixture of saturated alkyl groups averaging 12 carbon atoms; between dimethyl allyl amine and dodecyl chloroacetate; and between maleic anhydride and the reaction product of dimethylamino ethanol and lauryl bromide. Specific illustrations of these and other reactions will be given below in the following examples, together with illustrations of their use as monomeric emulsion stabilizers.

EXAMPLE 1.

Preparation and Use of Allyl Dodecyl Dimethyl Ammonium Chloride.

23 grams of dimethyl dodecyl amine were dissolved in 31 grams of H$_2$O and 9 grams of allyl chloride were added. After 6 hours stirring at 25°C some precipitation had occurred. 50 grams more H$_2$O were added and stirring was continued for 16 hours, resulting in a slightly cloudy homogeneous solution.

18 grams of this solution were dissolved in 290 grams of H$_2$O, and 100 grams of ethyl acrylate were emulsified therein by gradual addition with stirring. The pH of the emulsion was about 6.0. It was cooled to 17°C and 0.3 grams of 3% H$_2$O$_2$ in H$_2$O were added, followed by the dropwise addition of a reductant solution (0.02 grams of ferrous ammonium sulfate and 0.5 grams of ascorbic acid in 10 grams of H$_2$O). A nitrogen atmosphere was maintained throughout the polymerization in all examples, polymerization being initiated in the present instance after 1.8 grams of reductant solution had been added. The exotherm was 33°C in about two minutes. Addition of 2 grams more reductant and 2 grams more of 3% H$_2$O$_2$ after the reaction had cooled gave a 5°C exotherm. The yield of polymer formed was over 90% of theoretical, and no coagulum was formed.

Essentially similar results were obtained when the ethyl acrylate was replaced by a mixture of 10 parts of ethyl acrylate and 74 parts of 2-ethylhexyl acrylate. The above precedure was also repeated using dimethyl hexadecyl amine in place of dimethyl dodecyl amine, and using a mixture of 20 grams of vinyl acetate and 80 grams of 2-ethylhexyl acrylate as the principal monomer.

EXAMPLE 2.

Preparation and Use of Vinyloxyethyl Dimethyl Tridecyloxycarbonylmethyl Ammonium Chloride 28.8 grams of dimethylaminoethyl vinyl ether were dissolved in 98 grams of acrylonitrile. After cooling the solution to 15°C, 69.3 grams of tridecylchloroacetate were added with stirring. Stirring was continued for 72 hours at 25°C. Analysis showed 100% conversion to the quaternized ammonium chloride.

6 grams of the above solution were dissolved in 280 grams of H$_2$O, to which was added with stirring a mixture of 80 grams of ethyl acrylate, 10 grams of butyl acrylate, and 7 grams of acrylonitrile. The pH of the resulting emulsion was between 5.0 and 5.5. The emulsion was cooled to 17°C, after which polymerization was initiated and maintained using H$_2$O$_2$ and reductant as in Example 1. There was no coagulum formed in the resulting polymeric emulsion, and the yield was 92% of theoretical.

EXAMPLE 3.

Preparation and Use of Methacryloyloxyethyl Dimethyl Dodecyloxycarbonylmethyl Ammonium Chloride.

15.9 grams of dimethylaminoethyl methacrylate and 26.6 grams of dodecyl chloroacetate were stirred together in 45 grams of ethyl acetate at room temperature. After a short period of stirring, the white crystalline solid quaternary ammonium compound was formed, and was isolated.

3.0 grams of the above quaternary compound were dissolved in 350 grams of H$_2$O, to which a mixture of 10 grams of ethyl acrylate and 73.6 grams of 2-ethylhexyl acrylate were added with stirring. The pH of the resulting emulsion was 6.0. It was cooled to 18°C, and polymerization was initiated and maintained as in the above examples. The polymer yield was about 90%.

If the proper equivalents of dimethylaminoethyl methacrylate and tridecylchloroacetate are used to form the quaternized compound, the resulting methacryloyloxyethyl dimethyl tridecyloxycarbonylmethyl ammonium chloride acts as a monomeric emulsion stabilizer similar to its dodecyl homolog.

EXAMPLE 4.

Preparation and Use of Allyloxycarbonylmethyl Dimethyl Hexadecyl Ammonium Chloride.

13.5 grams of allyl chloroacetate were added with stirring to 26.9 grams of dimethyl hexadecyl amine in 40 grams of dimethyl formamide. Two layers were initially formed, but with continued stirring for 16 hours at 25°C, a clear, light yellow homogeneous solution was obtained. After 6 days standing, the solvent was removed under vacuum at 40°C. The resultant solid was washed with ethyl ether and dried. The product was somewhat greasy, and analysis showed 97% of the theoretical chloride content present.

Using the same general procedures as in the above examples, a mixture of 55 grams of vinyl acetate and 45 grams of butyl acrylate were emulsified using 3% of the weight of the above monomeric emulsifying agent, based on the weight of vinyl acetate and butyl acrylate, dissolved in 280 grams of $H_2O$. Polymerization was initiated and maintained as above by the use of $H_2O_2$ and reductant. The yield of polymer was 83%.

EXAMPLE 5.

Preparation and Use of Allyl Dodecylmorpholinium Bromide.

91.3 grams of N-cocomorpholine and 45 grams of allyl bromide were stirred in 306 grams of $H_2O$ at 25°C for 24 hours. The clear, colorless solution contained 96% of the theoretical yield of quaternized ammonium salt.

5 grams of the above 30% aqueous solution were dissolved in 1,000 grams of $H_2O$, and a mixture of 160 grams of ethyl acrylate, 20 grams of acrylonitrile, and 20 grams of butyl acrylate were added with stirring. The resultant emulsion was polymerized by the use of 0.3 grams of t-butyl peroxy maleic acid and 4.1 grams of the ferrous ammonium sulfate-ascorbic acid reductant solution. The yield of polymer was 96% of theoretical.

EXAMPLE 6.

Preparation and Use of 3-(4-Hydroxymaleoyl)-aminopropyl Dimethyl Tridecyloxycarbonylmethyl Ammonium Chloride This quaternary compound was prepared in two stages. 20.4 grams of dimethylamino propylamine were mixed with 55.4 grams of tridecyl chloroacetate in 75.8 grams of acrylonitrile. After 72 hours at 25°C, 90% of the theoretical chloride content was found in the form of the quaternized salt. The solution was cooled and 19.6 grams of crushed maleic anhydride were added, cooling being employed to keep the exothermic reaction below 22°C. 100% of the theoretical chloride ion was found by analysis.

6 grams of the above solution were dissolved in 280 grams of $H_2O$, and a mixture of 80 grams of ethyl acrylate, 10 grams of butyl acrylate, and 7 grams of acrylonitrile were added with stirring. The resulting emulsion, pH 4.0 to 4.5, was cooled, and polymerization was initiated and maintained by the $H_2O_2$-reductant system described in Example 1. Less than 1% of coagulum was formed, and the yield of polymer was 92%.

EXAMPLE 7.

Preparation and Use of 2-(4-Hydroxymaleoyloxy)ethyl Dimethyl p-Dodecylbenzyl Ammonium Chloride The preparation of this quaternary compound, like that of Example 6, was a two-stage reaction. 29.5 grams of p-dodecylbenzyl chloride and 8.9 grams of dimethylamino ethanol were mixed in 38.4 grams of acrylonitrile. After 24 hours at 25°C, 9.8 grams of crushed maleic anhydride were added to the clear solution. After 13 days' standing, the separated crystalline compound was washed with ethyl acetate and dried.

2.25 grams of the quaternary salt were dissolved in 290 grams of $H_2O$ and 75 grams of ethyl acrylate were added with stirring. The resultant emulsion was polymerized with the $H_2O_2$-reductant system used in previous examples. The yield of polymer was 96% of theoretical.

When lauryl bromide was used in the initial quaternization reaction in place of p-dodecylbenzyl chloride, followed by reaction with maleic anhydride, 2-(4-hydroxymaleoyloxy)ethyl dimethyl dodecyl ammonium bromide was produced. Its behavior as a monomeric emulsion stabilizer in the polymerization of ethyl acrylate was essentially similar to the behavior of 2-(4-hydroxymaleoyloxy)ethyl dimethyl p-dodecylbenzyl ammonium chloride.

EXAMPLE 8.

Preparation and Use of Methacryloyloxyethyl Dimethyl Hexadecyl Ammonium Bromide.

19.3 grams of 2-bromethyl methacrylate and 27.8 grams of dimethyl hexadecylamine were mixed at 25°C in 47.1 grams of acrylonitrile. After 6 days, 92% of the theoretical bromide was found in the form of the quaternized salt.

3 grams of the above solution diluted to 33% in acrylonitrile were added to 280 grams of $H_2O$. A mixture of 80 grams of ethyl acrylate, 10 grams of butyl acrylate, and 8 grams of acrylonitrile were added with stirring. Polymerization of the resultant emulsion was initiated and maintained by the $H_2O_2$-reductant system described in Example 1. The yield of polymer was 96%.

EXAMPLE 9.

Preparation and Use of Allyl Dimethyl Tridecyloxycarbonylmethyl Ammonium Chloride.

8.5 grams of dimethyl allylamine and 27.7 grams of tridecyl chloroacetate were mixed together in 36 grams of dimethyl formamide at 25°C. After 15 days' standing, petroleum ether was added to precipitate and isolate the crystalline product. Analysis showed that 85% of the theoretical chloride content was in the form of the quaternized salt.

5 grams of the quaternized compound were dissolved in 290 grams of $H_2O$, and 100 grams of ethyl acrylate were added with stirring. The resulting emulsion was polymerized by the customary $H_2O_2$-reductant system. The yield of usable polymer was over 90%.

When 26.3 grams of dodecyl chloroacetate were substituted for the 27.7 grams of the tridecyl chloroacetate, the dodecyl homolog of the above-described monomeric emulsion stabilizer was prepared. Its function and behavior are the same as that of the tridecyl compound.

EXAMPLE 10.

Preparation and Use of Vinyloxyethyl Dimethyl p-Dodecylbenzyl Ammonium Chloride.

11.5 grams of dimethylaminoethyl vinyl ether and 29.5 grams of p-dodecylbenzyl chloride were stirred together in 41 grams of acrylonitrile at 25°C for 24 hours. The chloride by analysis was found to be completely quaternized.

2.5 grams of the above solution were dissolved in 700 grams of $H_2O$. A mixture of 200 grams of ethyl acrylate, 25 grams of butyl acrylate, and 24 grams of acrylonitrile were added with stirring. The resultant emulsion was polymerized using a total of 35 grams of 3% $H_2O_2$ and 11 grams of the reductant solution of Example 1. No coagulum was formed, and the polymer yield was 91% of theoretical.

EXAMPLE 11.

Preparation and Use of 3-Methacryloyloxy 2-Hydroxypropyl Dimethyl Octadecyl Methyl Ammonium Sulfate.

Equimolar quantities of N-methyl-N-octadecyl amine and glycidyl methacrylate were reacted together in methanol to form methacryloyloxyhydroxypropyl methyl octadecyl amine. 14.3 grams of the resultant amine were dissolved in 20 grams of dimethyl formamide and 4.2 grams of dimethyl sulfate were added slowly with stirring. After 10 days' standing at 25°C, 9 grams of crystalline material was isolated, washed with ether, and dried. The sulfate band in the crystalline product was identified in the I.R. spectrum.

2.25 grams of the above stabilizer were dissolved in 290 grams of $H_2O$. 75 grams of ethyl acrylate were added with stirring. Polymerization was initiated and maintained by the usual $H_2O_2$-reductant system. Less than 1 gram of coagulum formed, and the polymer yield was 96% of theoretical.

EXAMPLE 12.

Preparation and Use of Allyl Hexadecyl Dimethyl Ammonium Fluoride.

Allyl hexadecyl dimethyl ammonium chloride was prepared by reacting allyl chloride and dimethyl hexadecyl amine as set forth in Example 1. 17.8 grams of the chloride in 23.5% aqueous solution were treated with a stoichiometric excess of AgF in aqueous solution until analysis of the filtrate showed only a trace of chloride ion present. Excess silver ion was removed by the careful addition of NaCl, AgCl being removed by filtration.

64 grams of ethyl acrylate, 8 grams of butyl acrylate, and 8 grams of acrylonitrile were emulsified by gradual addition with stirring to 2.4 grams (3% by weight) of the allyl hexadecyl dimethyl ammonium fluoride in 120 grams of $H_2O$. The pH of the emulsion was about 6.0. It was cooled to 20°C and 10 grams of 3% aqueous $H_2O_2$ were added, followed by the dropwise addition of the reductant solution of Example 1 until polymerization was initiated after 5 grams of reductant had been added. The exotherm was 10°C in 13 minutes. A total of 14 grams of reductant and 13 grams of aqueous $H_2O_2$ were used to complete the polymerization. No coagulum was formed and the polymer yield was 95%.

EXAMPLE 13.

Preparation of Allyl Hexadecyl Dimethyl Ammonium Iodide.

16.8 grams of allyl iodide were dissolved in 44.6 grams of ethyl acetate and 27.8 grams of dimethyl hexadecyl amine were added slowly with stirring at room temperature. Within 15 minutes after the addition of the amine was complete, the viscosity of the solution increased and crystallization occurred. After 24 hours the crystals were filtered, washed with ethyl acetate, and dried. The colorless crystalline product contained 88% of the theoretical amount of iodide ion.

The proportion by weight of monomeric emulsion stabilizer used to stabilize the polymerization of other ethylenically-unsaturated monomers will depend on the nature of the latter. In general, 0.1% to 10% of stabilizer is used, with a preferred range of 1% to 5%. In the case where ethyl acrylate is the major monomer, 0.5% of emulsion stabilizer will generally result in a satisfactory polymerization. In the case of 2-ethylhexyl acrylate, the amount of stabilizer is increased to from 3% to 5%.

Ethylenically-unsaturated monomers suitable for copolymerizing with the monomeric emulsion stabilizers of this invention comprise vinyl acetate, vinyl chloride, acrylonitrile, and acrylic monomers in general represented by the general formula

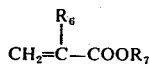

where $R_6$ is a hydrogen atom or a methyl group, and $R_7$ is a saturated alkyl radical of 1 to 14 carbon atoms. As is known in the art of preparing acrylic ester polymers, the softness of the polymer and the difficulty of initiating polymerization increase as the number of carbon atoms in the ester group increases. In the practice of this invention, when the acrylic monomer contains more than 8 carbon atoms in the ester group, it is advantageous to mix therewith at least about 20% of an acrylic ester with fewer than 4 carbon atoms in the ester group to initiate polymerization and enhance the stability of the dispersion. Therefore, esters in which the ester group contains from 1 to 4 carbon atoms are preferred.

Mixtures of more than one such ethylenically-unsaturated monomer may be used, and in order to impart special properties of toughness, rigidity, or cross-linking reactivity to the polymer, a minor proportion, usually less than 20 mole percent, of the major monomer may be replaced by some other ethylenically-unsaturated monomer such as vinyl esters, typified by vinyl laurate and vinyl stearate; vinyl ethers such as vinyl methyl ether, vinyl ethyl ether, and vinyl butyl ether; di-unsaturated monomers such as diethylene glycol diacrylate, ethylene glycol diitaconate, diallyl phthalate, divinyl benzene and the like; acrylic and methacrylic acids, acrylamide and methacrylamide, hydroxyethyl acrylate and methacrylate, and hydroxypropyl acrylate and methacrylate, and styrene.

Although the above examples using the stabilizers of this invention relate to batch processing, their use is equally well adapted to continuous polymerization processes.

Having thus described our invention, we claim:

1. Compounds corresponding to the formula

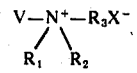

wherein V is selected from the class consisting of vinyl acetoxy, (CH$_2$=CH—O—CO—CH$_2$—), allyl acetoxy, (CH$_2$=CH—CH$_2$—O—CO—CH$_2$—), and methallyl acetoxy (CH$_2$=C(CH$_3$)—CH$_2$—O—CO—CH$_2$—) groups;

R$_1$ and R$_2$ are selected from the class consisting of benzyl groups and alkyl groups of from 1 to 7 carbon atoms; R$_3$ is a lipophilic saturated aliphatic hydrocarbon group of from 7 to 28 carbon atoms; and X is a radical selected from the class consisting of F$^-$, Cl$^-$, Br$^-$, I$^-$, [CH$_3$SO$_4^-$, C$_2$H$_5$SO$_4^-$,] and

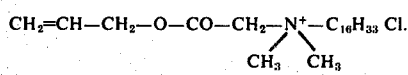

2. The compound according to claim 1 wherein R$_1$ and R$_2$ are methyl groups.

3. The compound according to claim 1 wherein the compound is allyloxycarbonylmethyl dimethyl hexadecyl ammonium chloride, CH$_2$=CH—CH$_2$—O—CO—CH$_2$—N$^+$—C$_{16}$H$_{33}$ Cl.
                                    / \
                                  CH$_3$  CH$_3$

* * * * *